US009561062B2

(12) United States Patent
Hayes et al.

(10) Patent No.: US 9,561,062 B2
(45) Date of Patent: Feb. 7, 2017

(54) SPONDYLOLISTHESIS REDUCTION SYSTEM

(71) Applicant: Alphatec Spine, Inc., Carlsbad, CA (US)

(72) Inventors: Kyle Hayes, Mission Viejo, CA (US); Wally Gillespie, Carlsbad, CA (US)

(73) Assignee: ALPHATEC SPINE, INC., Carlsbad, CA (US)

( * ) Notice: Subject to any disclaimer, the term of this patent is extended or adjusted under 35 U.S.C. 154(b) by 0 days.

(21) Appl. No.: 13/835,938

(22) Filed: Mar. 15, 2013

(65) Prior Publication Data

US 2013/0245692 A1    Sep. 19, 2013

Related U.S. Application Data

(60) Provisional application No. 61/612,919, filed on Mar. 19, 2012.

(51) Int. Cl.
*A61B 17/88* (2006.01)
*A61B 17/70* (2006.01)
*A61B 17/02* (2006.01)

(52) U.S. Cl.
CPC .......... *A61B 17/708* (2013.01); *A61B 17/025* (2013.01); *A61B 2017/0256* (2013.01)

(58) Field of Classification Search
CPC ..... A61B 17/88; A61B 17/56; A61B 17/1764; A61B 17/68; A61B 17/8872
USPC .............. 606/86 A, 90, 99, 105, 250–279
See application file for complete search history.

(56) References Cited

U.S. PATENT DOCUMENTS

2005/0245928 A1* 11/2005 Colleran et al. ............... 606/61
2010/0274252 A1* 10/2010 Bottomley et al. ............ 606/90

* cited by examiner

*Primary Examiner* — Mary Hoffman
*Assistant Examiner* — Tara R Carter
(74) *Attorney, Agent, or Firm* — Michael J. Loi

(57) ABSTRACT

A system for reducing deformities in the spine includes a first tower assembly and a second tower assembly. The first tower assembly includes a first tower that couples to a first screw in a first vertebral level, a load transfer ring rotatable coupled to the first tower, and a load transfer link rotatably coupled to the load transfer ring. The second tower assembly includes a second tower that couples to a second screw in a second vertebral level, a load applicator secured to the second tower, and a load transfer member rotatably coupled to the second tower and linked to the load transfer link. The load applicator applies force to the load transfer member to position the first tower assembly relative to the second tower assembly.

7 Claims, 18 Drawing Sheets

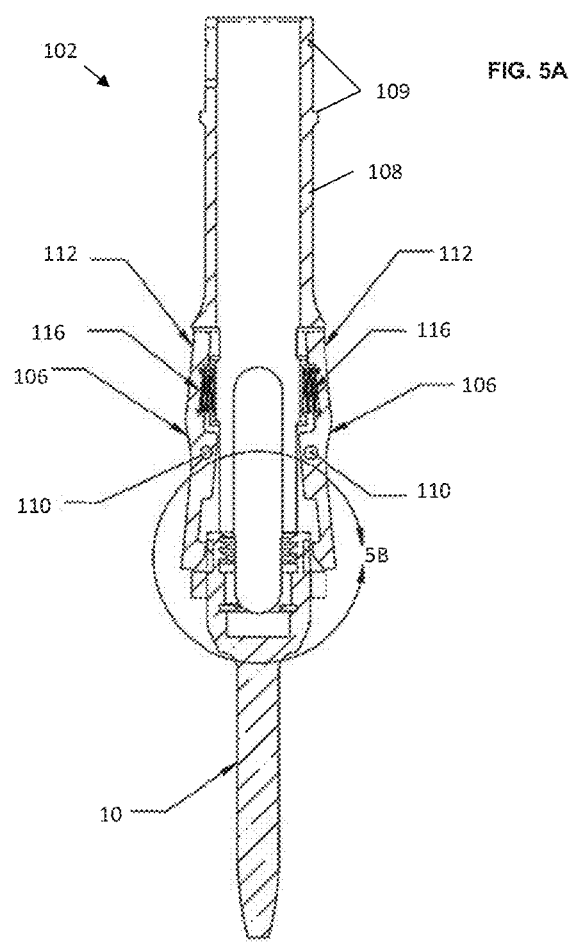
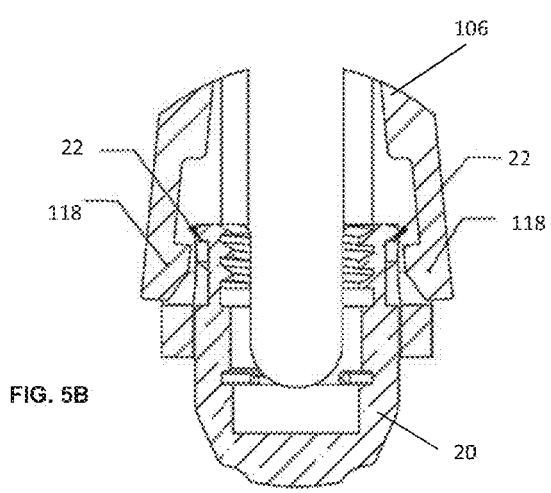

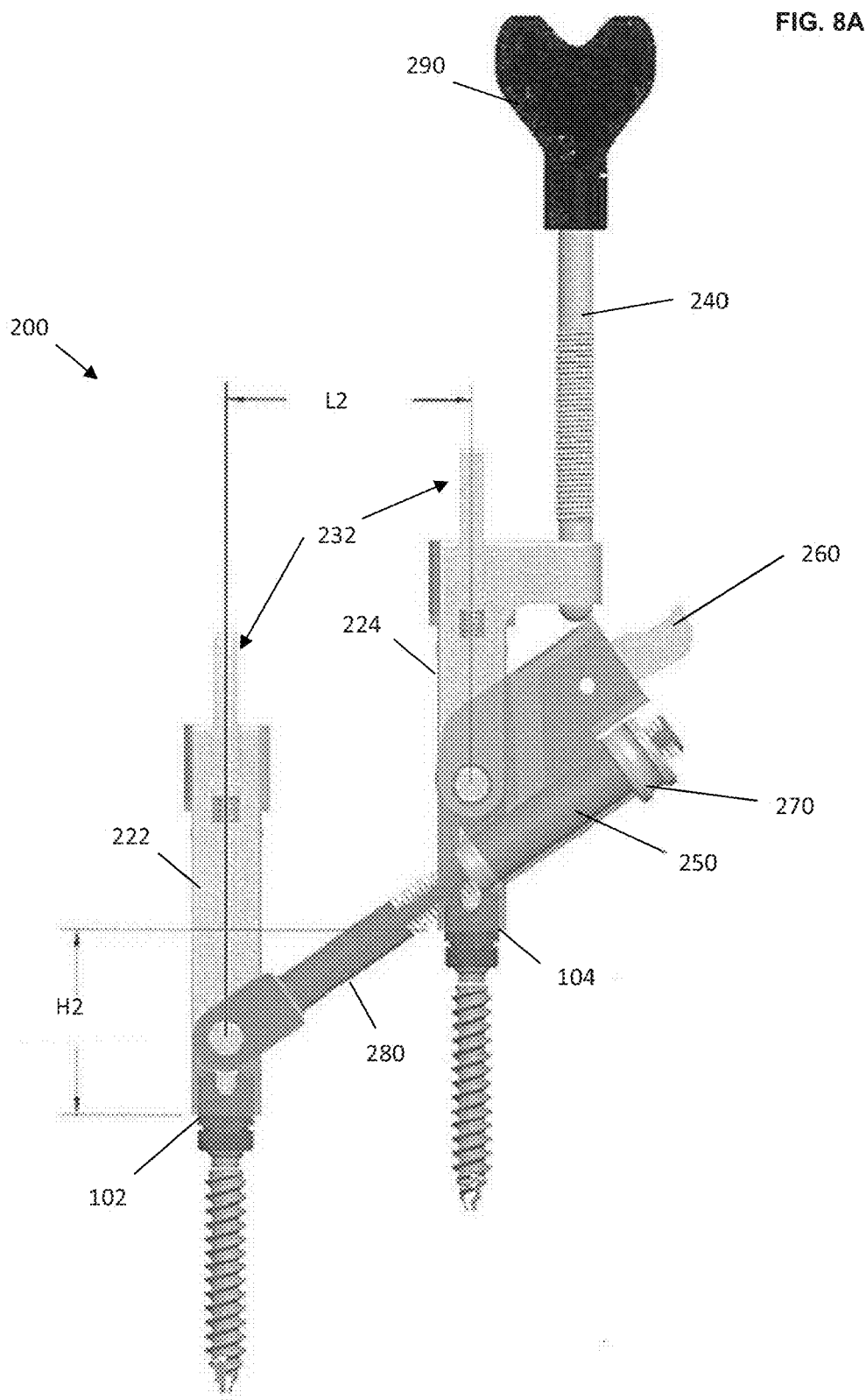

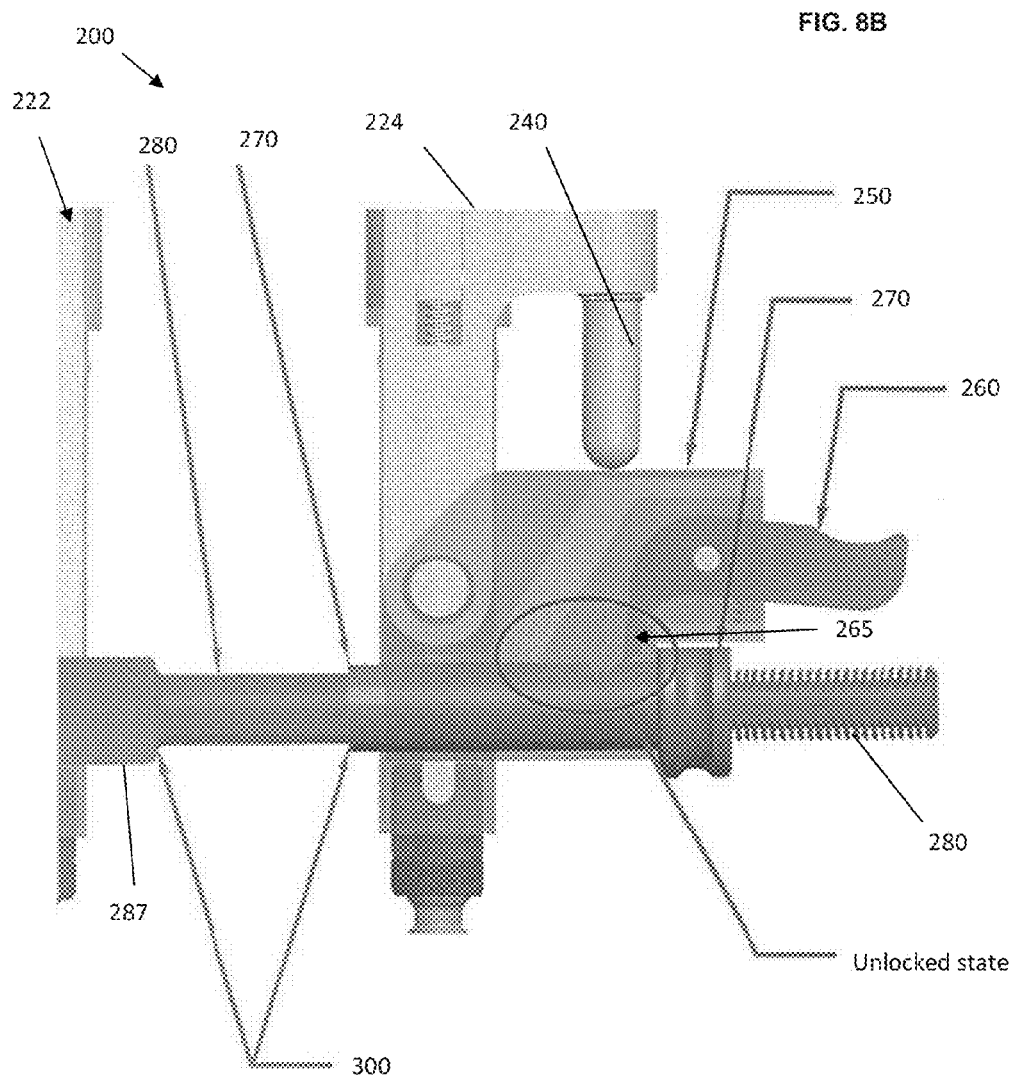

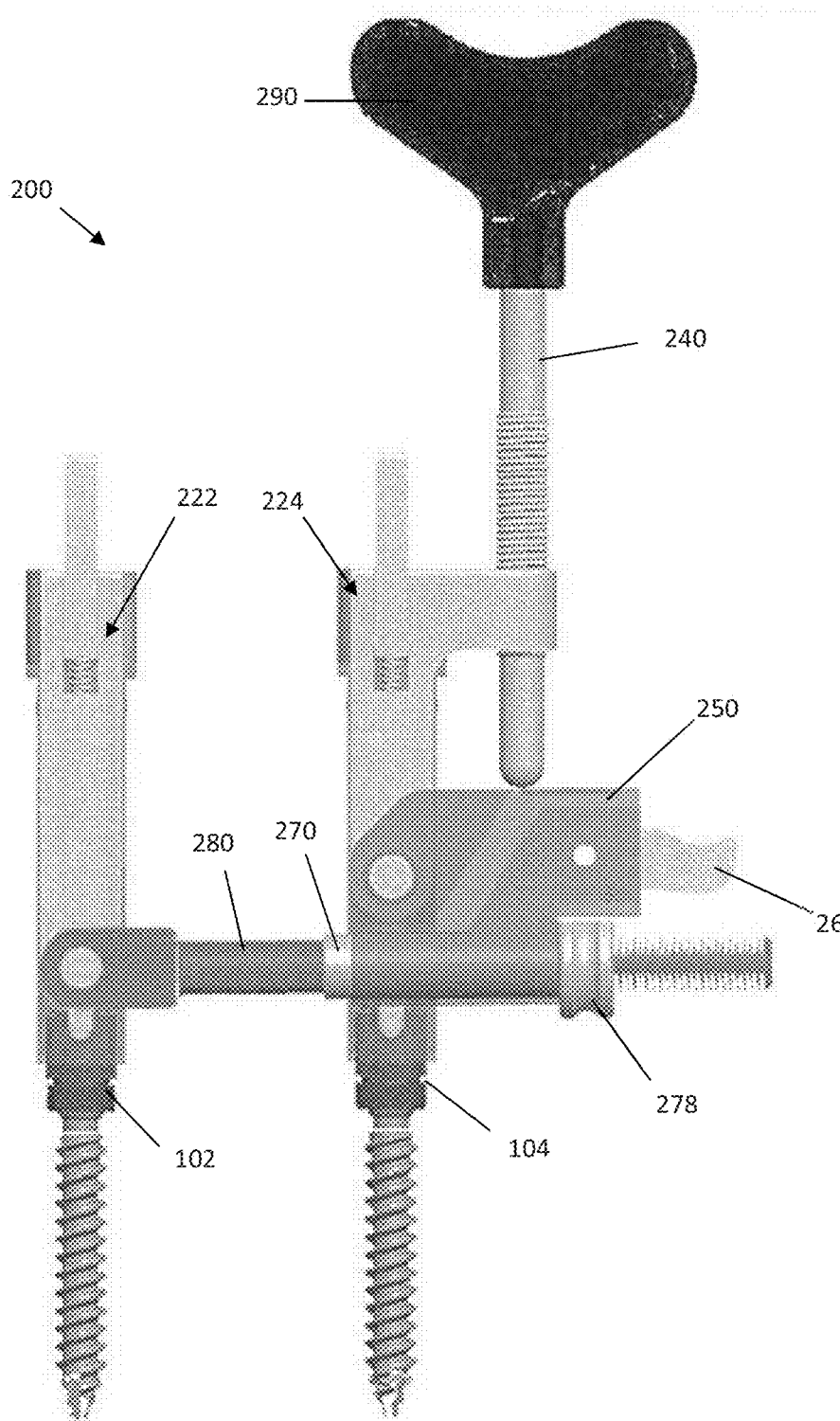

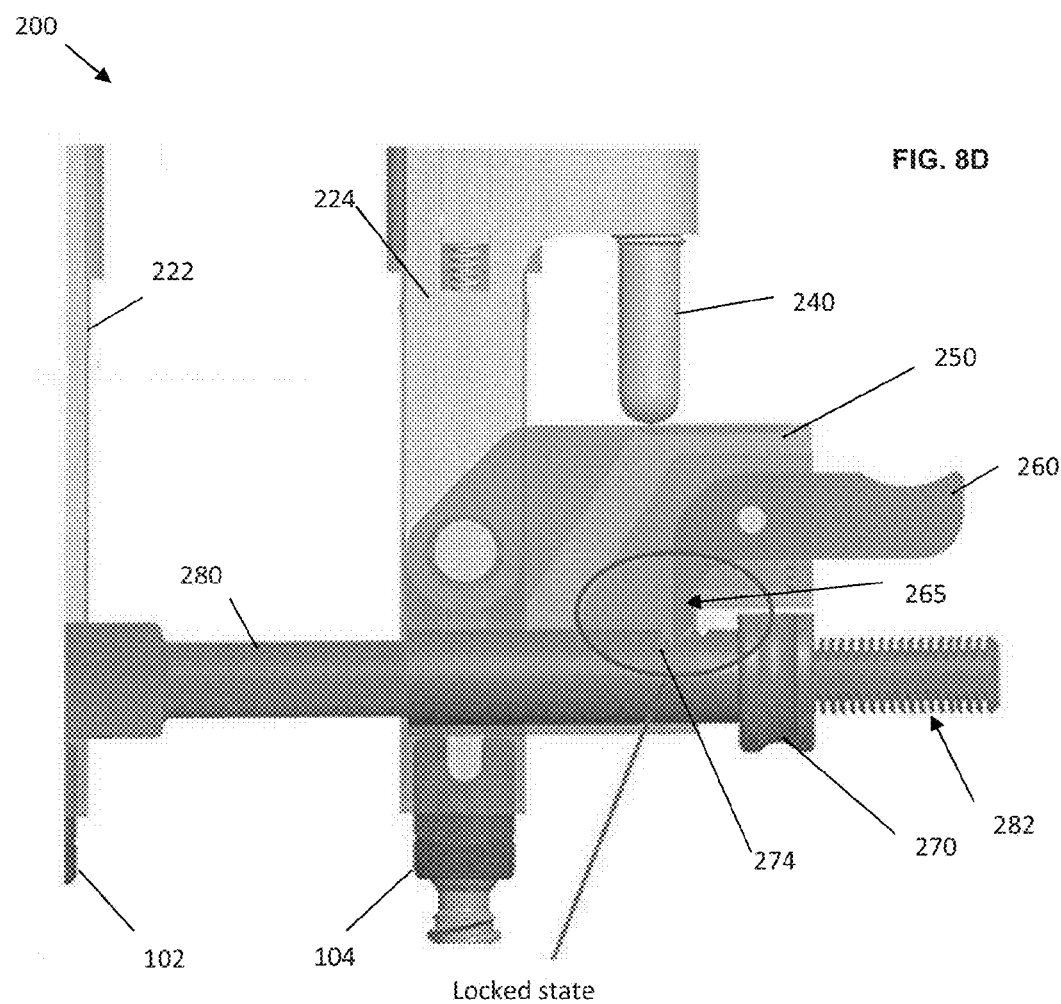

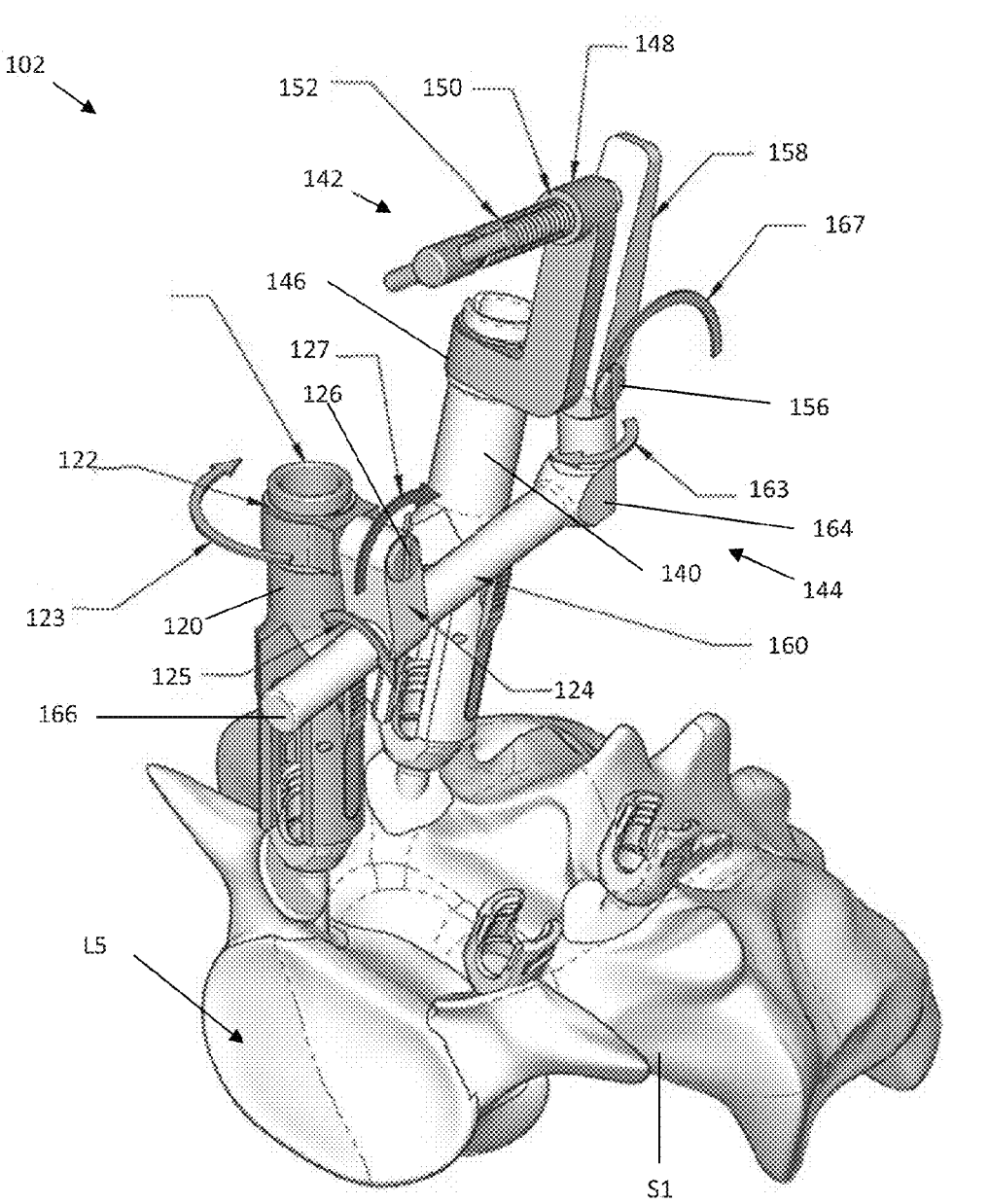
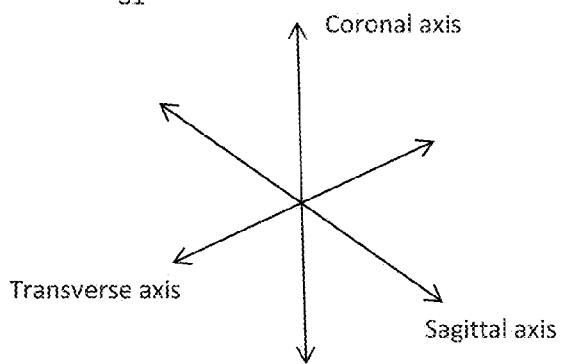
FIG. 9

SPONDYLOLISTHESIS REDUCTION SYSTEM

CROSS-REFERENCE TO RELATED APPLICATIONS

The present application claims priority to U.S. Provisional Application Ser. No. 61/612,919, filed Mar. 19, 2012, which is herein incorporated by reference in its entirety.

The present disclosure generally relates to the field of spinal orthopedics, and more particularly to instruments for reducing spondylolisthesis.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

Spondylolisthesis is the anterior or posterior displacement of a vertebra of the vertebral column in relation to the vertebra below. In the lower region of the back where the lumbar vertebrae meet the sacrum, spondylolisthesis may occur more frequently. For example, at the L5-S1 level, the fifth lumbar vertebra may slip forward or in the anterior direction relative to the first level of the sacrum. Treatment for spondylolisthesis depends on the severity of the slippage. For severe cases, surgical correction is required.

Various systems and methods are known to alleviate and correct spondylolisthesis. For example, German Patent 41 27 303, filed Aug. 17, 1991 (also disclosed in European Patent No. 0528177, filed Jul. 16, 1992) to Aesculap AG, discloses such a device. Other devices include U.S. Pat. No. 6,565,568, filed Sep. 28, 2000 to Rogozinski and U.S. Pat. Pub. No. 2009/0216237, filed Jun. 30, 2006 to Frezal et al. However, some of these systems may be difficult to maneuver, attach, and remove from screw heads. Some of these systems may make it difficult to insert and secure fixation rods after correcting the slippage without removing portions of the systems.

SUMMARY

A system for reducing deformities in the spine includes a first tower assembly and a second tower assembly. The first tower assembly includes a first tower that couples to a first screw in a first vertebral level, a load transfer ring rotatable coupled to the first tower, and a load transfer link rotatably coupled to the load transfer ring. The second tower assembly includes a second tower that couples to a second screw in a second vertebral level, a load applicator secured to the second tower, and a load transfer member rotatably coupled to the second tower and linked to the load transfer link. The load applicator applies force to the load transfer member to position the first tower assembly relative to the second tower assembly.

BRIEF DESCRIPTION OF THE DRAWINGS

FIGS. 4A-5B are cross-sectional views of a tower assembly of the system and one of the bone screws according to the principles of the present disclosure.

FIG. 8A is a side view of the first and second tower assemblies mounted with the first and second mounts in the unreduced state; FIG. 8B is enlarged side view of the of the first and second tower assemblies mounted with the first and second mounts in the unlocked state; FIG. 8C is a side view of the first and second tower assemblies mounted with the first and second mounts in the reduced state; and FIG. 8D is an enlarged side view of the first and second tower assemblies mounted with the first and second mounts in the locked state.

FIG. 9 is a perspective view of a right side of the system including the first and the second tower assemblies of FIGS. 6-7 according to the principles of the present disclosure.

DETAILED DESCRIPTION

Figure 1A:
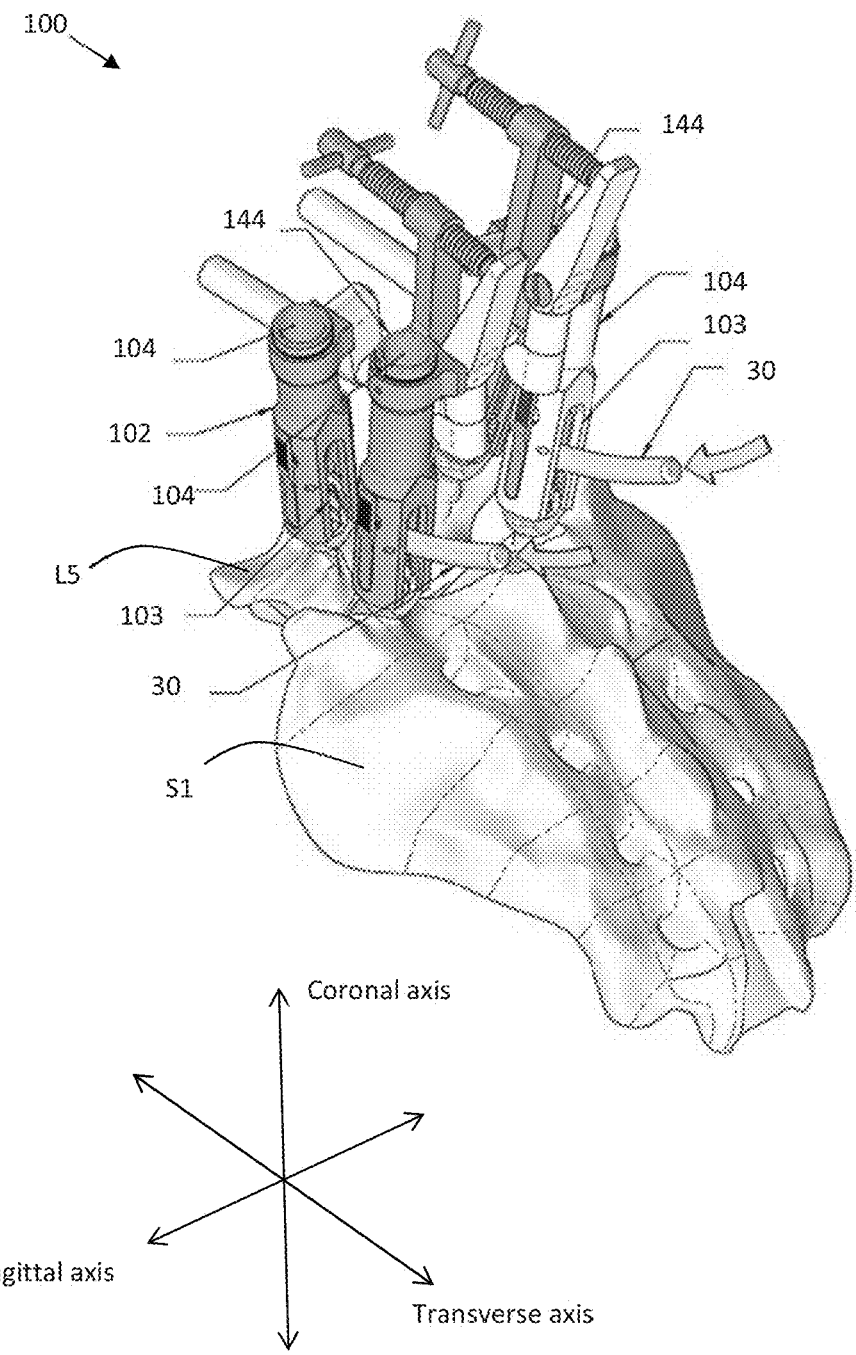
FIG. 1A is a perspective view of a system for reducing deformities in the spine according the principles of the present disclosure.

For a mid to high grade spondylolisthesis at the L5-S1 level, the anatomy is exposed and bone screws are placed in the pedicles of the L5 lumbar vertebra bilaterally near the cephalad end of the sacrum. Bone screws are also placed in the sacrum. A system of instruments may be used to reposition the L5 vertebra relative to the S1 level. The system may comprise a set of mirrored tower assemblies which attach to the tops of the screw heads. The tower assemblies which attach to the lumbar bone screws comprise a tower, a ring attached to the tower which may rotate about the longitudinal axis of the tower, and a link attached to the ring which may rotate about an axis at right angles to the tower's longitudinal axis. The tower assemblies which attach to the sacral bone screws each comprise a tower, a pivoting level, and a drive screw.

The sacral towers may provide a relative ground reference for the reduction apparatus while the lumbar towers may act as load transfer structures. A drive apparatus mounted to the sacral towers provides forced to produce the necessary anatomical correction. The tower assemblies transmit the leverage generated by the drive apparatus into a posterior load on the L5 vertebral body. The system applies a generally posteriorly directed force to the vertebral body while allowing the vertebral body to travel posteriorly along a path of least resistance. The system may not dictate an exact path the vertebral body takes during the reduction procedure. Rods can then be placed in the heads of the bone screws and secured in place without removing the system.

Benefits of the present invention include the ability to attach the tower assemblies and remove them from the screw head in a single action. The present invention also provides the ability to insert fixation rods and secure them with set screws without removing the towers. The present invention also allows the vertebral body to travel along a path of least resistance rather than dictating a path that may include interference from the sacrum, vertebral disc, or other tissues.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Reference to the invention may also be described with respect to coronal, sagittal, and transverse axes of the body. The coronal axis refers to an axis running substantially from front (anterior) to back (posterior) of the body and extending through the mid-section. The sagittal axis refers to an axis running substantially from left to right of the body and extending through the mid-section to intersect the coronal axis at a right angle. The transverse axis refers to an axis running substantially from head to toe of the body and crossing the point where the coronal and sagittal axes intersect at a right angle. Furthermore, the coronal, sagittal, and transverse planes refer to the standard definitions associated with each term. Namely, the coronal plane being a plane perpendicular to the coronal axis and formed by the transverse and sagittal axes, the sagittal plane being perpendicular to the sagittal axis and formed by the coronal and transverse axes, and the transverse plane being perpendicular to the transverse axis and formed by the sagittal and coronal axes.

Referring to FIGS. 1-10, a system 100 for correcting spondylolisthesis is shown in conjunction with two sets of bone screws inserted into two vertebrae of a spinal column. As shown in FIG. 1a, the system 100 may include first tower assemblies 102 and second tower assemblies 104. The tower assemblies 102 and 104 may be attached to bone screws at the distal end of the tower assemblies 102 and 104. For example, in FIGS. 2 and 3, a first set of bone screws 10 has been inserted into a fifth lumbar vertebra L5 and a second set of bone screws 12 has been inserted into the first level of the sacrum S1 through a minimally invasive surgery (MIS) technique. The system 100 may be used in conjunction with a spinal fixation system that includes one or more fixation rods 30 disposed through a lumen 103 of the tower assemblies 102 and 104 and setscrews (not shown) to permanently align and rigidly fix two or more levels of the spinal column such as the L5 and S1 levels. Exemplary bone screws and fixation systems may be found in U.S. Pub. No. 2010/0036443 and U.S. Pub. No. 2009/0171391 both of which are incorporated herein by reference in their entirety.

Although the system 100 of the present disclosure is described herein with reference to the L5 and S1 levels, the system 100 may be used in other regions of the spine where spondylolisthesis or other slippage of vertebral bodies may occur. As shown in FIG. 1a, the tower assemblies 102 and 104 may removably couple with sets of bones screws 10 and 12 respectively via MIS procedures. The tower assemblies 102 and 104 include a load transfer member 144 on the proximal end 104 of the tower assemblies 102 and 104 to transmit a leverage generated by the drive apparatus to cause relative movement of the tower assembly 102 from tower assembly 104. The first tower assembly 102 may be referred to as a lumbar tower assembly. The second tower assembly 104 may be referred to as a sacral tower assembly. The tower assemblies 102 and 104 may couple to the bone screws 10 and 12 respectively and in substantially similar fashion.

Figure 1B:
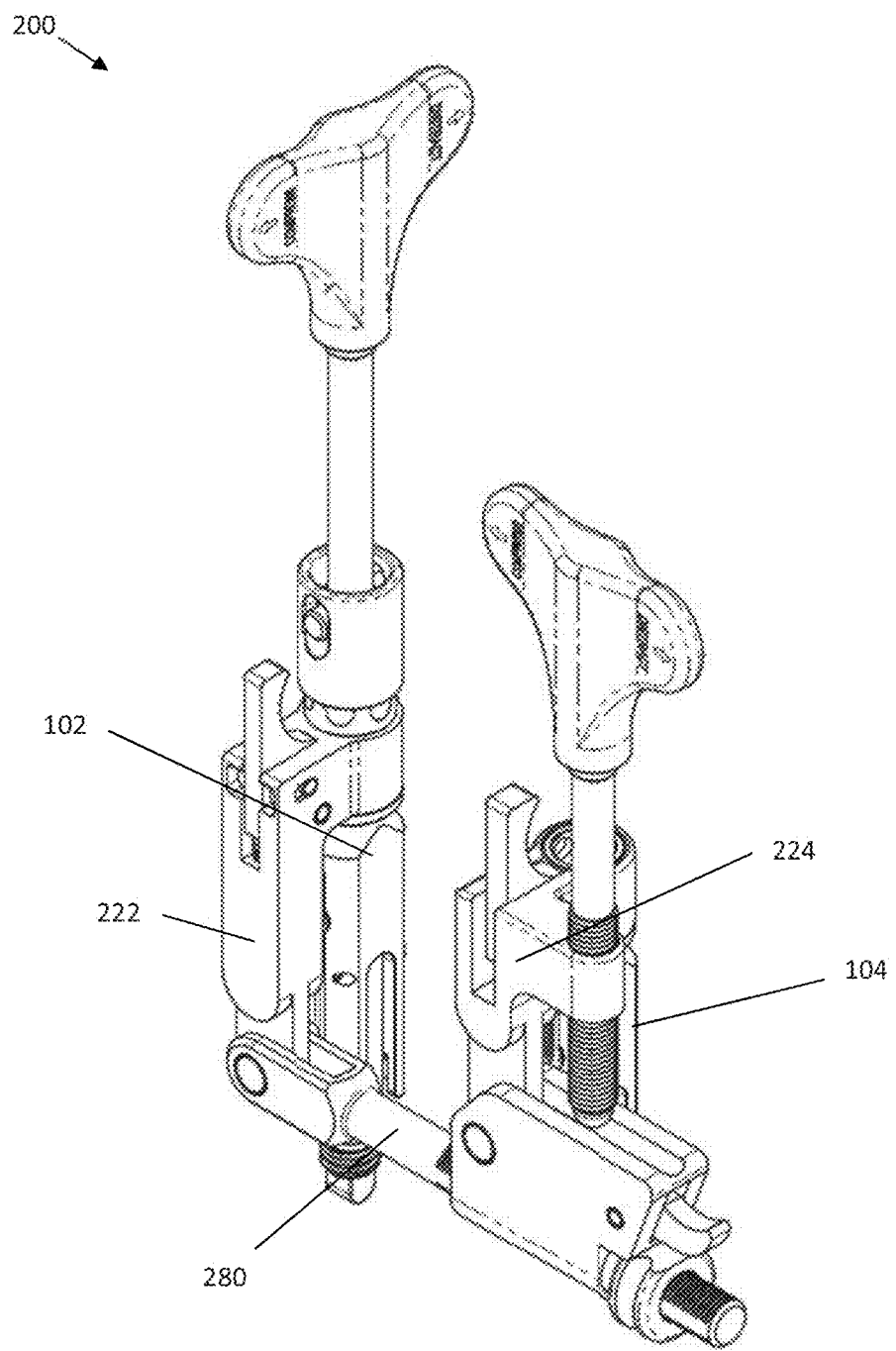
FIG. 1B is a perspective view of alternative embodiment of the first and second mount.

An alternative system 200 is shown in FIG. 1b, where the first tower assembly 102 includes a first mount 222 and the second tower assembly 104 includes a second mount 224. The first mount 222 operably coupled to the proximal end of the first tower assembly 102, and the second mount 224 is operably coupled to the proximal end of the second tower assembly 104. A load reduction arm 280 is operably coupled to the first mount 222 and second mount 224 to transmit a leverage and cause relative movement of the first tower assembly 102 from second tower assembly 104 to a locked state and a reduced state.

Figure 2:
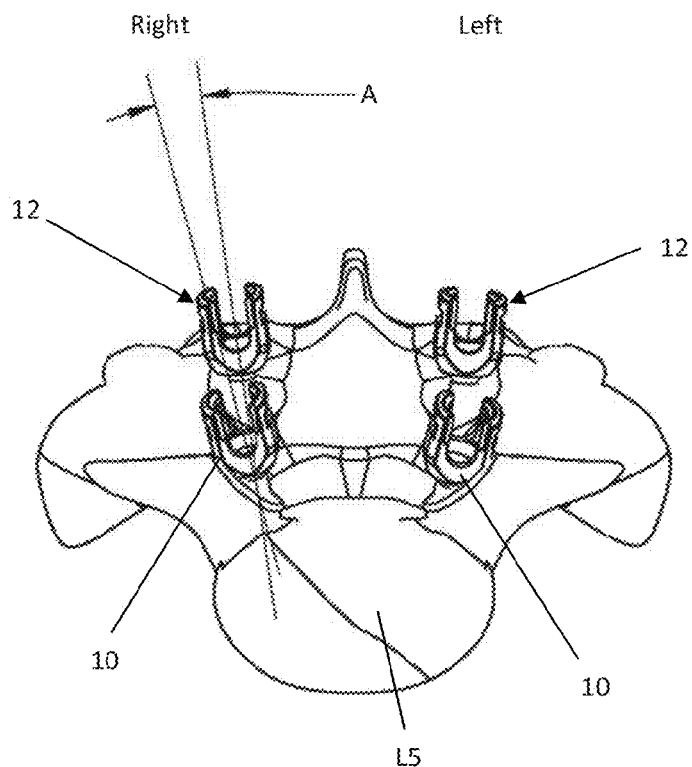
FIG. 2 is top view of a portion of the spine and associated bone screws for use with the system according to the principles of the present disclosure.
Figure 3:
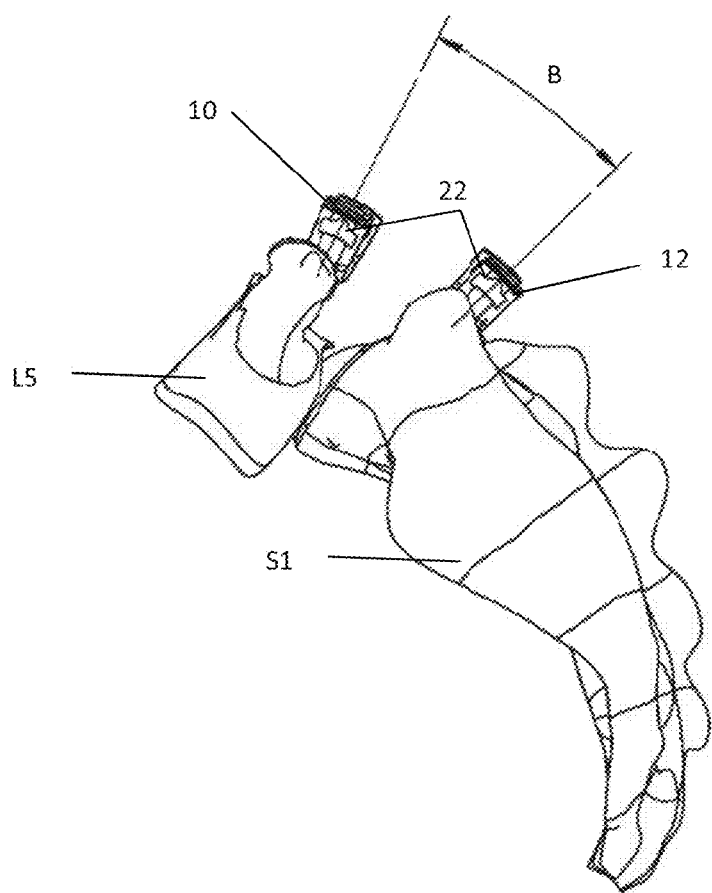
FIG. 3 is a side view of the portion of the spine and associated bone screws of FIG. 2 according to the principles of the present disclosure.
Figure 4A:
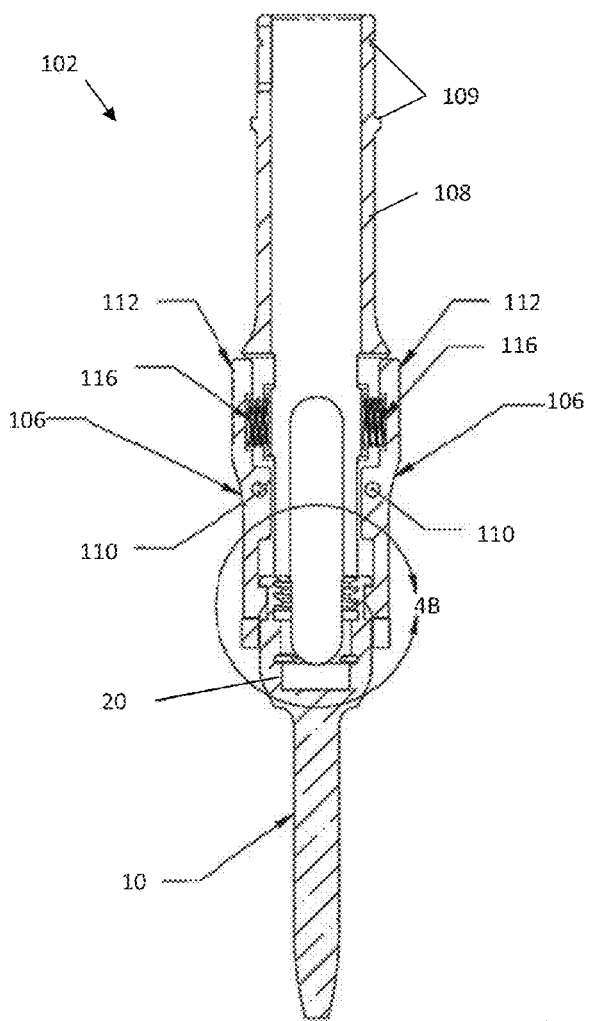
Figure 4B:
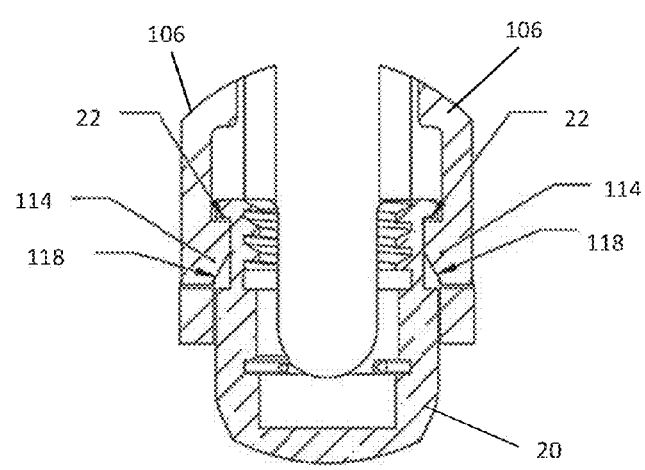

Anatomy and the degree of severity of the spondylolisthesis will vary from patient to patient. Thus, after placement of the bone screws 10, 12, longitudinal axes of the bone screws 10, 12 may not be co-planer when observed from a viewpoint normal to the transverse plane as shown by FIG. 2. For example, an angle A may be formed by the axes. Additionally, an angle between the longitudinal axes may vary when observed from a viewpoint normal to the sagittal plane as shown by FIG. 3. For example, an angle B may be formed by the axes. To accommodate for the variations between patients and severity of the spondylolisthesis, various interconnecting elements of the system 100 provide sufficient degrees of freedom to allow for variations in placement and actuation of the system 100. Each tower assembly 102 and 104 may include additional features that enable positioning and alignment of the L5 vertebra relative to the S1 level of the sacrum prior to fixation with the rods 30. Because each set of tower assemblies includes mirrored components, references throughout this description may refer to left sides and right sides of the system 100 interchangeably. Left and right may indicate the left side and right side from the viewpoint of a patient. Furthermore, each left and right tower assembly 102 and 104 may couple with the bone screws in substantially similar fashion.

As shown in FIGS. 4A-5B, a portion of one tower assembly is shown in conjunction with one of the bone screws. For ease of discussion, the description herein will refer to one of the lumbar tower assemblies 102 and one of the L5 vertebra bone screws 12. The lumbar tower assembly 102 may include features to enable single-action coupling with and removal from a receiving portion 20 of the bone screw 10. For example, the lumbar tower assembly 102 may include clips 106 in sidewalls 108 of the tower assembly 102. The clips 106 may extend along the length of the sidewall and may pivot on pins 110. Each clip 106 may include a proximal end with grips or pads 112 which may be depressed by the surgeon to actuate the clip 106. Each clip 106 may include a distal end with a projection 114, such as a boss or protrusion that extends radially inward from the clip 106. The projection 114 may engages with a recessed portion 22, such as a bore, pocket, or indentation, of the receiver portion 20 of the bone screw 10. A bias mechanism 116, such as a coil spring, leaf spring, or other elastic mechanism, may position the clip 106 into an engaged or closed position with the receiver portion 20. The surgeon may apply force via the pads 112 to position the clip 106 into a disengaged or open position, wherein the projection 114 disengages the receiver portion 20, thus permitting removal of the tower assembly 102 from the screw 10. The projection 114 may include a ramped surface 118 or taper to facilitate coupling with the receiver portion 20 without actuating the clips 116 to the open position. The proximal end of the tower assemblies 102 and 104 may also include a mating feature 109 as to allow the load transfer member 144 to be operably coupled to the proximal end of the tower assemblies 102 and 104. The mating feature 109 may protrude into the surface of the sidewalls 108 and may also protrude outwards from the surface of the sidewalls 108, as to provide a lipped and indented mating feature 109 with a space therebetween.

Figure 6A:
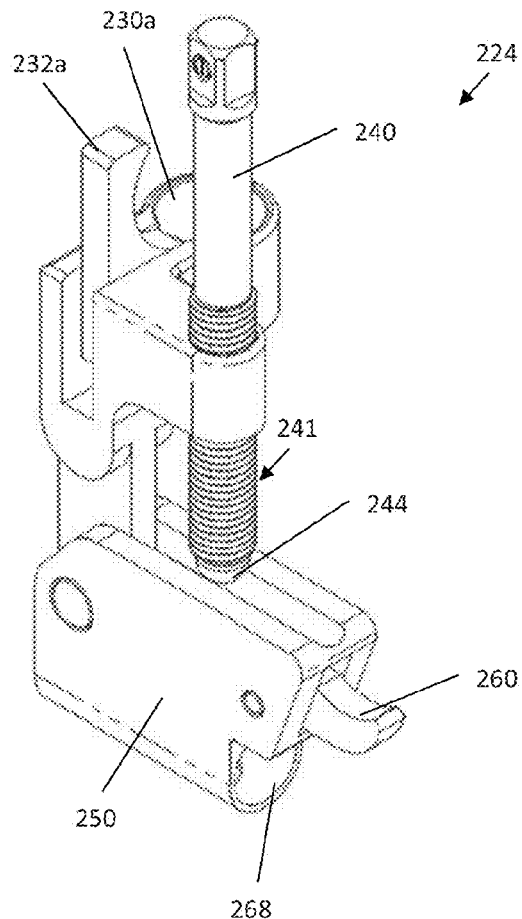
FIG. 6A is a perspective view of the second mount.
Figure 6E:
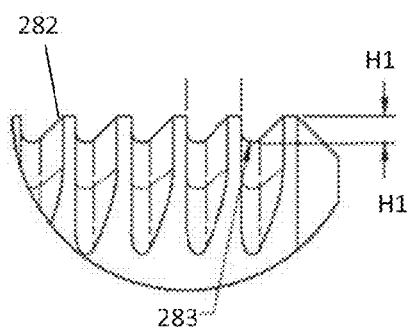
FIG. 6E is an enlarged view of section 6E from FIG. 6D showing the ratcheted portion of the load reduction arm.
Figure 6D:
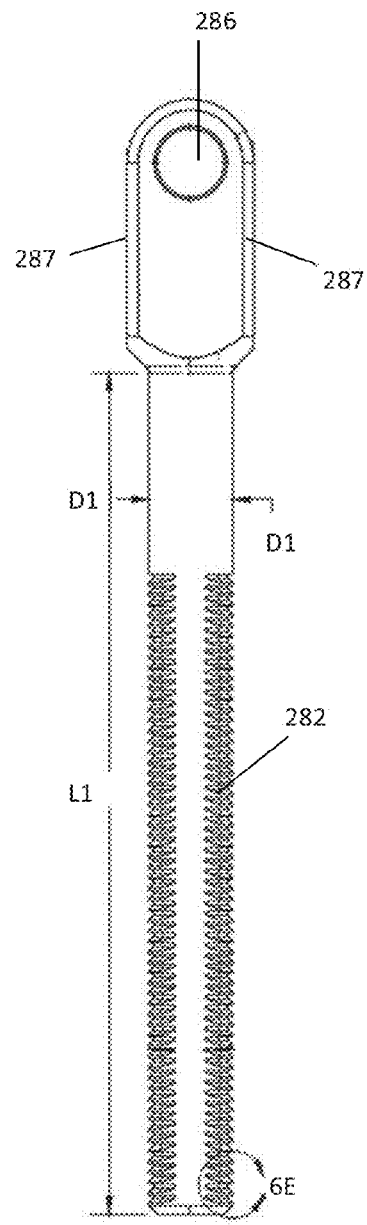
FIG. 6D is a side view of the load reduction arm.
Figure 6B:
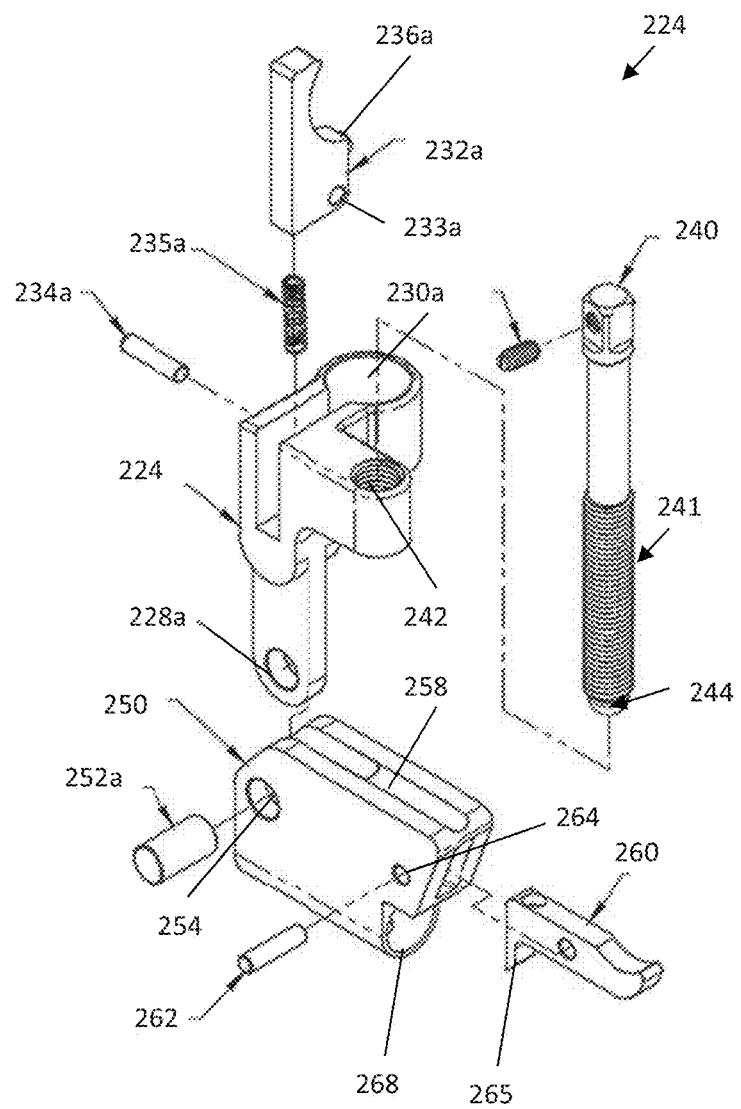
FIG. 6B is perspective exploded of the second mount.

Referring to FIGS. 6A-6B, the second mount 224 includes a load transfer ring 230a for mounting the second mount 222 on the proximal end of the second tower assembly 104. A mounting trigger 232a may be operably coupled with the load transfer ring 230a as to lock the proximal end of the tower assembly 104 in place. The mounting trigger 232a may be rotatably coupled to the proximal end of the second mount 224 by way of an opening 233a, a pin 234a, and a spring 235a. The mounting trigger 232a may include a locking feature 236 as to mate with the mating feature 109 on the proximal end of the sidewalls 108 of the first and second tower assemblies 102, 104. The locking feature 236 and the load transfer ring 230a may secure the second mount 224 to the second tower assembly 104. The second mount 224 also includes a reduction drive shaft 240 that is operably coupled with a drive shaft bore 242 mounted on the proximal end of the second mount 224. The reduction drive shaft 240 includes a substantially threaded portion 241 along the exterior of the reduction drive shaft 240 to operably couple with a threaded portion along the interior of the drive shaft bore 242. The reduction drive shaft 240 is substantially parallel with the load transfer ring 230a and the tower assembly 104. The distal end 244 of the reduction drive shaft 240 operably engages a distraction slide lock 250 on the distal end of the second mount 224. The reduction drive shaft 240 may be advanced along its longitudinal axis by operation of the threaded engagement as to displace a second end of the distraction slide lock 250. The first end of the distraction slide lock 250 is rotatably engaged with the distal end of the second mount 224 by way of a pin 252a. The distal end of the second mount 224 includes a pin opening 228a and the distraction slide lock 250 includes a pin opening 254 to permit rotation movement of the distraction slide lock 250 about its first end. A top portion 258 of the distraction slide lock 250 engages the distal end 244 of the reduction drive shaft 240 as to permit the distal end 244 to slide along the top portion 258 and displace the second end of the distraction slide lock 250. In one embodiment, the top portion 258 is a curved portion as to engage the distal end 244.

Figure 6C:
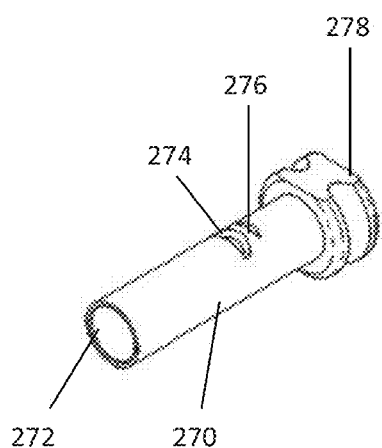
FIG. 6C is perspective view of the locking tube.

A distraction trigger 260 is operably coupled on the second end of the distraction slide lock 250 by way of a trigger pin 262 and a trigger opening 264. The distraction trigger 260 includes a locking feature 265 as to lock the distraction slide lock 250 in place by a locking tube 270 (as shown in FIG. 6C) displaced within the lock bore 268 that traverses the bottom portion of the distraction slide lock 250. The locking tube 270 includes a central lumen 272 traversing the length of the locking tube 270, a recess opening 274 traversing the surface and communicating with the central lumen 272, a recess 276 displaced into the surface of the locking tube 270, and a stop feature 278 on the second end. The stop feature 278 on the second end of the locking tube 270 includes a circumference that is greater than the lock bore 268, as to prevent the locking tube 270 from moving towards the first end of the distraction slide lock 250. The locking feature 265 operably engages the recess opening 274 and traverses the thickness of the locking tube 270 as to mate with the load reduction arm 280.

Referring to FIG. 6D, the load reduction arm 280 includes a central shaft with a diameter D1 that is less than the diameter of the locking tube 270, such that the central shaft may longitudinally move through the locking tube 270. The load reduction arm 280 includes a ratcheted portion 282 along the central shaft to the second end of the load reduction arm 280. As shown in FIG. 6E, the ratcheted portion 282 includes stepped features 283 as to mate with the locking feature 265. In one embodiment, the stepped features 283 include a height H1 that mates with at least a portion of the locking feature 265. The load reduction arm 280 includes a length L1, which may be determined by the length between vertebrae to be displaced. The first end of the load reduction arm 280 includes raised features 287 that are a greater diameter than D1. The first end of the load reduction arm 280 includes an opening 286 to be rotatably coupled with the first mount 222.

Figure 6F:
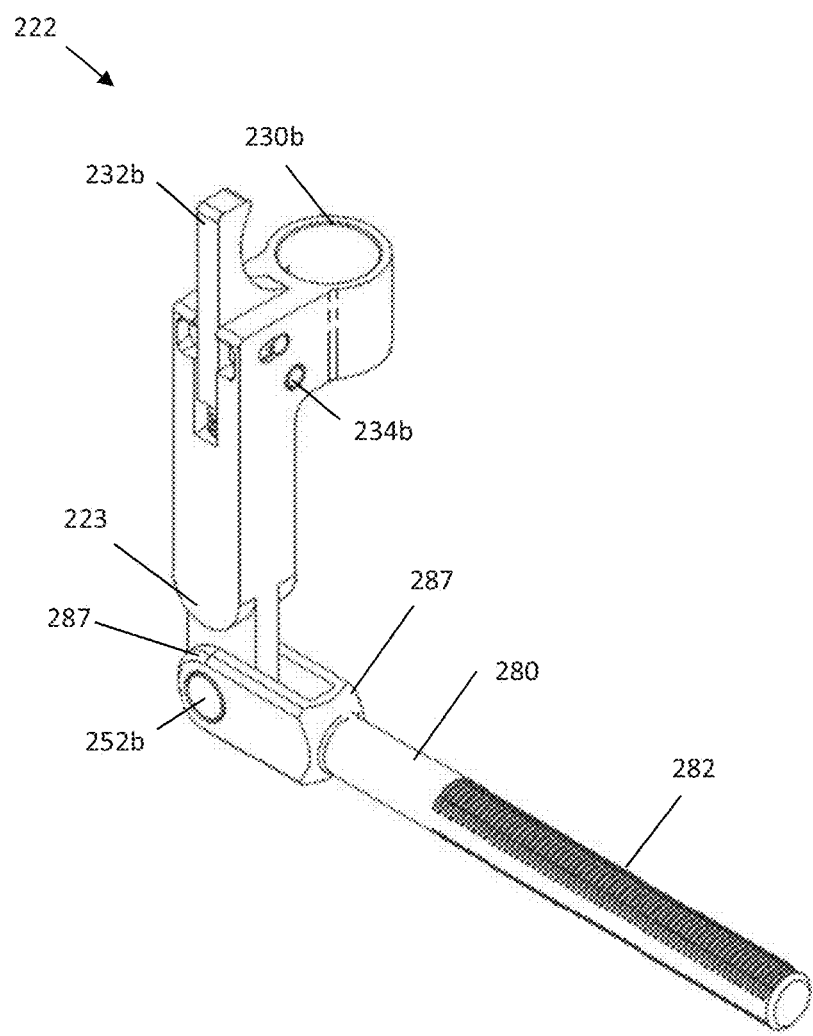
FIG. 6F is a perspective view of the first mount.
Figure 6G:
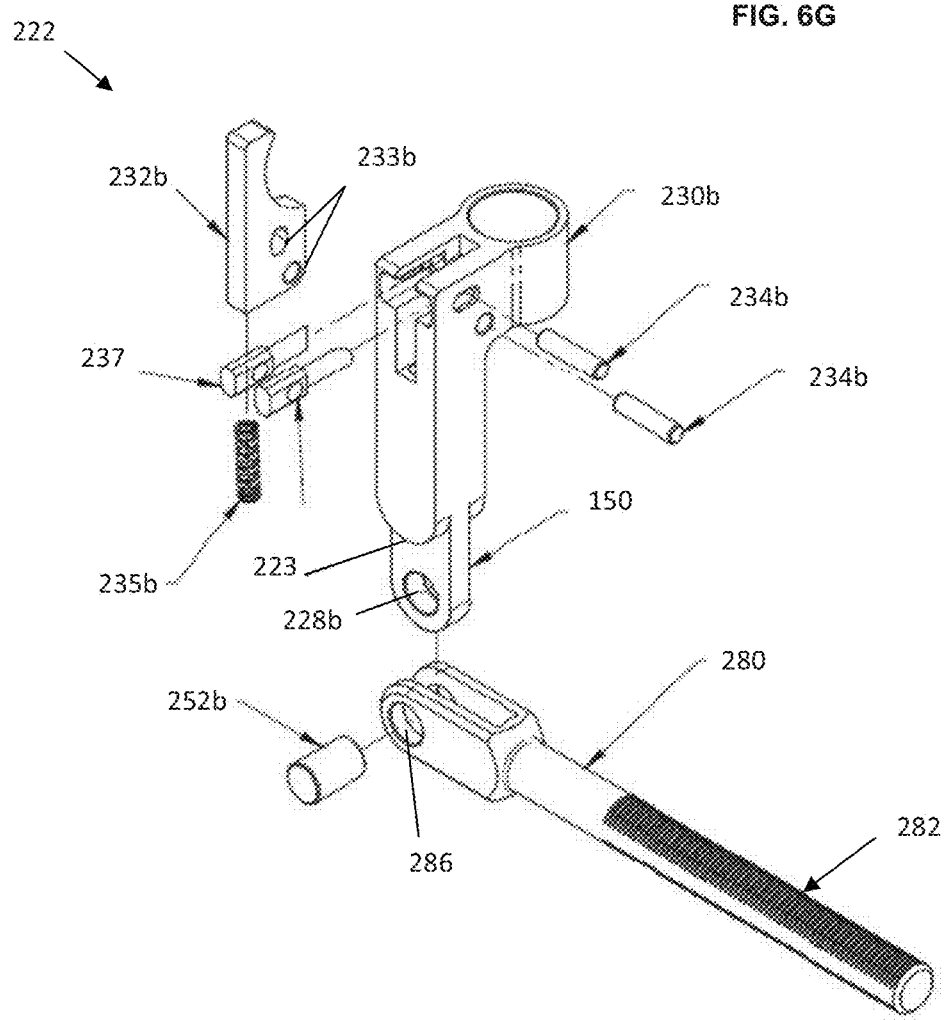
FIG. 6G is an exploded perspective view of the first mount.

Referring to FIGS. 6F-6G, the first mount 222 includes the load reduction arm 280 rotatably coupled to the distal end of the first mount 222 by way of an opening 228b and a pin 252b operably coupled through the opening 286 of the load reduction arm 280. Similar to the second mount 224, the first mount 222 includes a load transfer ring 230 on the proximal end of the first mount 222. The proximal end of the first mount 222 includes a trigger 232b that may be operably coupled with the load transfer ring 230b as to lock the proximal end of the tower assembly 102 in place. The mounting trigger 232b may be rotatably coupled to the proximal end of the first mount 222 by way of openings 233b, pins 234b, a spring 235b, and tabs 237. The mounting trigger 232a may include a locking feature as to mate with the mating feature 109 on the proximal end of the sidewalls 108 of the first and second tower assemblies 102, 104. The locking feature and the load transfer ring 230b may secure the first mount 222 to the first tower assembly 102. The distal end of the first mount 222 also includes at least one profiled tab 223, which permit the raised features 287 of the load reduction arm 280 to rotate. The load reduction arm 280 may displace the first mount 222 along its longitudinal axis.

Figure 7A:
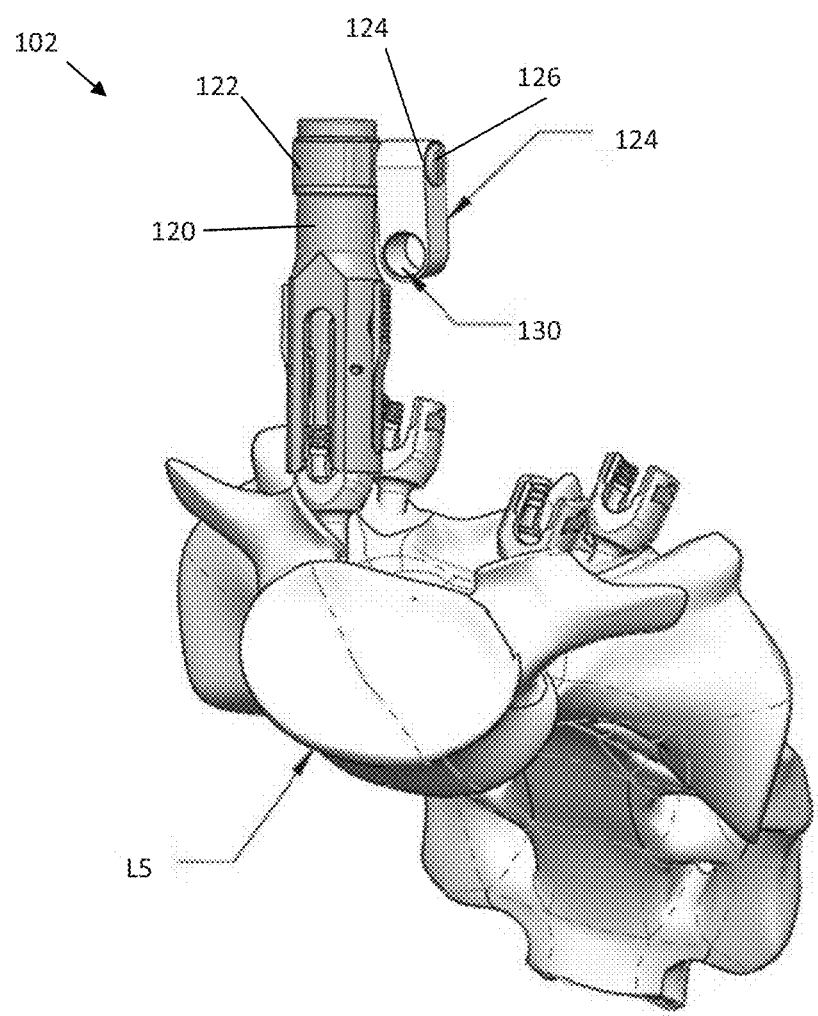
FIG. 7A is a perspective view of a first tower assembly of the system according to the principles of the present disclosure.

Continuing now with FIG. 7A, the lumbar tower assembly 102 includes additional features that link to the sacral tower assembly 104. Once linked, the sacral tower assembly 104 may be used to apply forces on the lumbar tower assembly 102 to reposition the L5 vertebra. For example, the lumbar tower assembly 102 may include a lumbar tower 120, a load transfer ring 122, and a load transfer link 124. The transfer ring 122 may be rotatably coupled to the proximal end of the lumbar tower 120. The transfer ring 122 may rotate about a longitudinal axis of the lumbar tower 120. A transfer post 126 may extend radially from the transfer ring 122 and perpendicular to the longitudinal axis of the lumbar tower 120. The transfer link 124 may be rotatably coupled to the lumbar tower 120 by the transfer post 126 of the transfer ring 122. For example, the transfer link 124 may include a first bore 128 at its proximal end that slides over the transfer post 126. The transfer link 124 may rotate about the longitudinal axis of the transfer post 126. A second bore 130 may extend through a distal end of the transfer link 124 and perpendicular to the transfer post 126. The second bore 130 may be configured to receive additional features of the system that connect with the sacral tower assembly 104 as described herein.

Figure 7B:
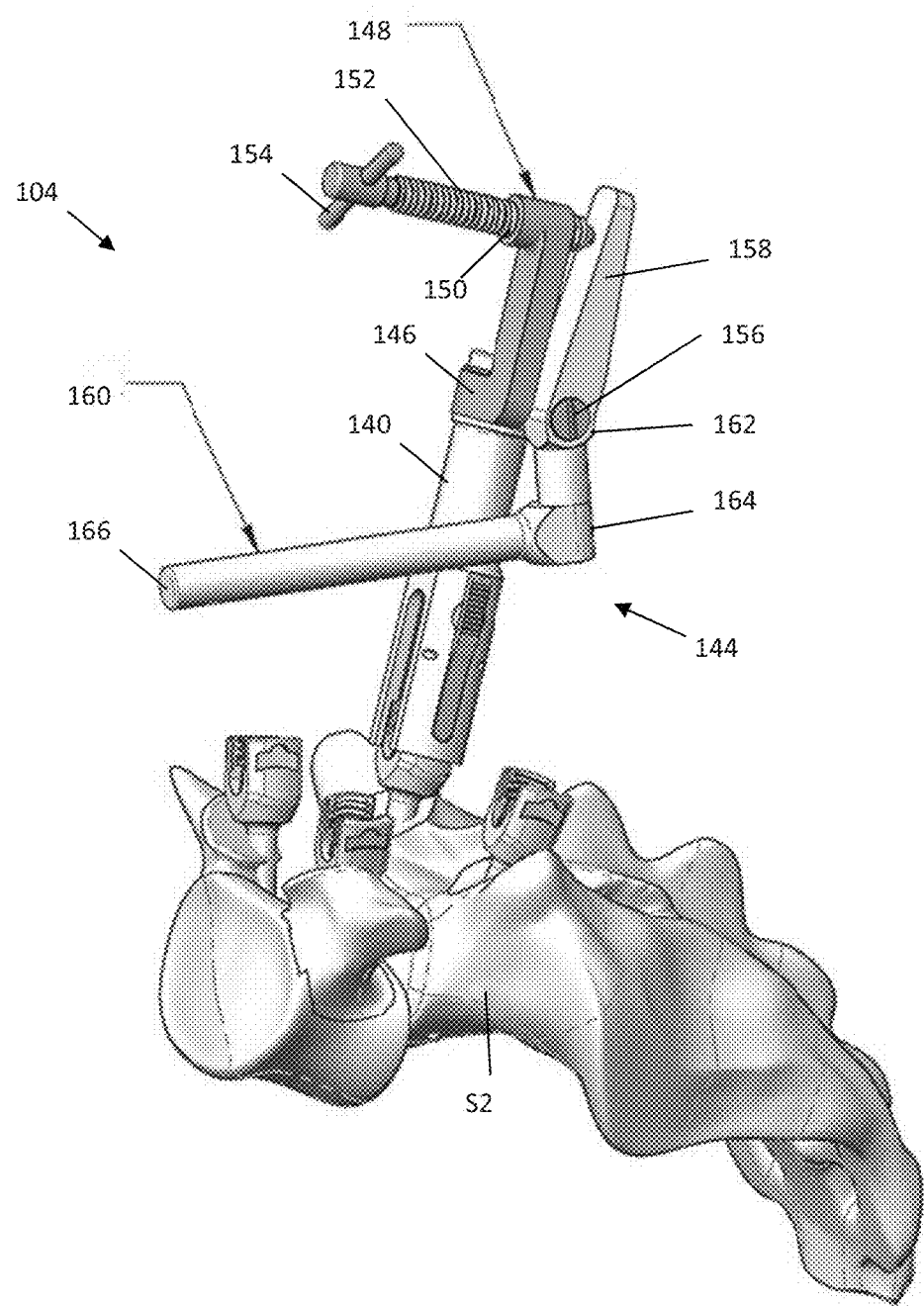
FIG. 7B is a perspective view of a second tower assembly of the system according to the principles of the present disclosure.

Referring now to FIG. 7B, the sacral tower assembly 104 includes additional features that link to the lumbar tower assembly 102. For example, the sacral tower assembly 104 may include a sacral tower 140, load applicator 142, and a load transfer member 144. The load applicator 142 may include a load ring 146 that rotatably couples to a proximal end of the second tower 140. The load ring 146 may rotate about the longitudinal axis of the second tower 140. The load ring 146 may be secured to the second tower 140 via a set screw (not shown.) An extension member 148 may extend proximally from the load ring 146 and parallel to the longitudinal axis of the second tower 140. The extension member 148 may include a thru-bore 150 at its proximal end configured to receive the load applicator 142. For example, the load applicator 142 may include a threaded shaft 152 and a handle 154. The thru-bore 150 may include threads configured to engage the threaded shaft 152 on the load applicator 142. The surgeon may rotate the handle 154 to advance the threaded shaft 152 through the thru-bore 150.

A second post 156 may extend radially or tangentially from the load ring 146 and connect with features of a load transfer member 144 as described below. For example, the load transfer member 146 may include a receiving portion 158 and a linking portion 160 that connect the first tower assembly 102 with the second tower assembly 104. The receiving portion 158 engages with the threaded shaft 152 of the load applicator 142. For example, the load applicator 142 may extend through the thru-bore 150 to engage with a proximal end of the receiving portion 158. At a distal end of the receiving portion 158, a thru-bore 162 provides pivotal connection with the second post 156. The linking portion 160 extends away from the distal end of the receiving portion 158 to form a substantially "L" shaped load transfer member 146. The linking portion 160 may rotatably couple to the receiving portion 158 at a first end 164. A second end 166 of the linking portion 160 may cantilever away from the receiving portion 158 to engage with the transfer link 124.

Referring now to FIGS. 8A-8B, the tower assemblies 102 and 104 are attached to the first mount 222 and the second mount 224 for the alternative system 200. The screws are placed on the towers and are inserted in a minimally invasive fashion, and then the first and second mounts 102, 102 are attached to the top or proximal ends of the tower assemblies 102 and 102 by the mounting triggers. The displaced vertebrae may be separated by a height H2 and a length L2. FIG. 8A shows the alternative system 200 in the unreduced state where the load reduction arm 280 can move freely during the reduction until the distraction slide lock 250 is locked via the locking tube 270 and the distraction trigger 260. The L5 vertebrae may be reduced into position by levering off of the placed screw in the S1 vertebrae, and the reduced state of the alternative system is shown in FIG. 8C. Distraction can be applied before or after reduction of the L5 vertebrae and the distraction may also be held in place by the reduction drive shaft 240 and operation of a handle 290 operably coupled to the proximal end of the reduction drive shaft 240. As shown in FIG. 8B, the alternative system 200 is in the unlocked state where the first end of the locking tube 270 sticks out at least a portion beyond the distraction slide lock 250, and the reduction arm 280 can slide freely while the distraction trigger 260 and locking feature 265 remains engaged in the recess 276 behind the recess opening 274. A hand held distractor (not shown) is placed at position 300 between the raised feature 287 of the load reduction arm 280 and the first end of the locking tube 270 and a distraction load is applied, which causes the locking tube 270 to move until the stopping feature 278 abuts or bottoms out against the face of the second end of the distraction slide lock 250, as shown in FIGS. 8C-8D. Once the stopping feature 278 of the locking tube 270 abuts the second end of the distraction slide lock 250, the distraction trigger 260 drops into the recess opening 274 of the locking tube 270, and the locking feature 265 engages the ratcheted portion 282 to hold the distraction in the locked state until released, as shown in FIG. 8D.

Figure 10A:
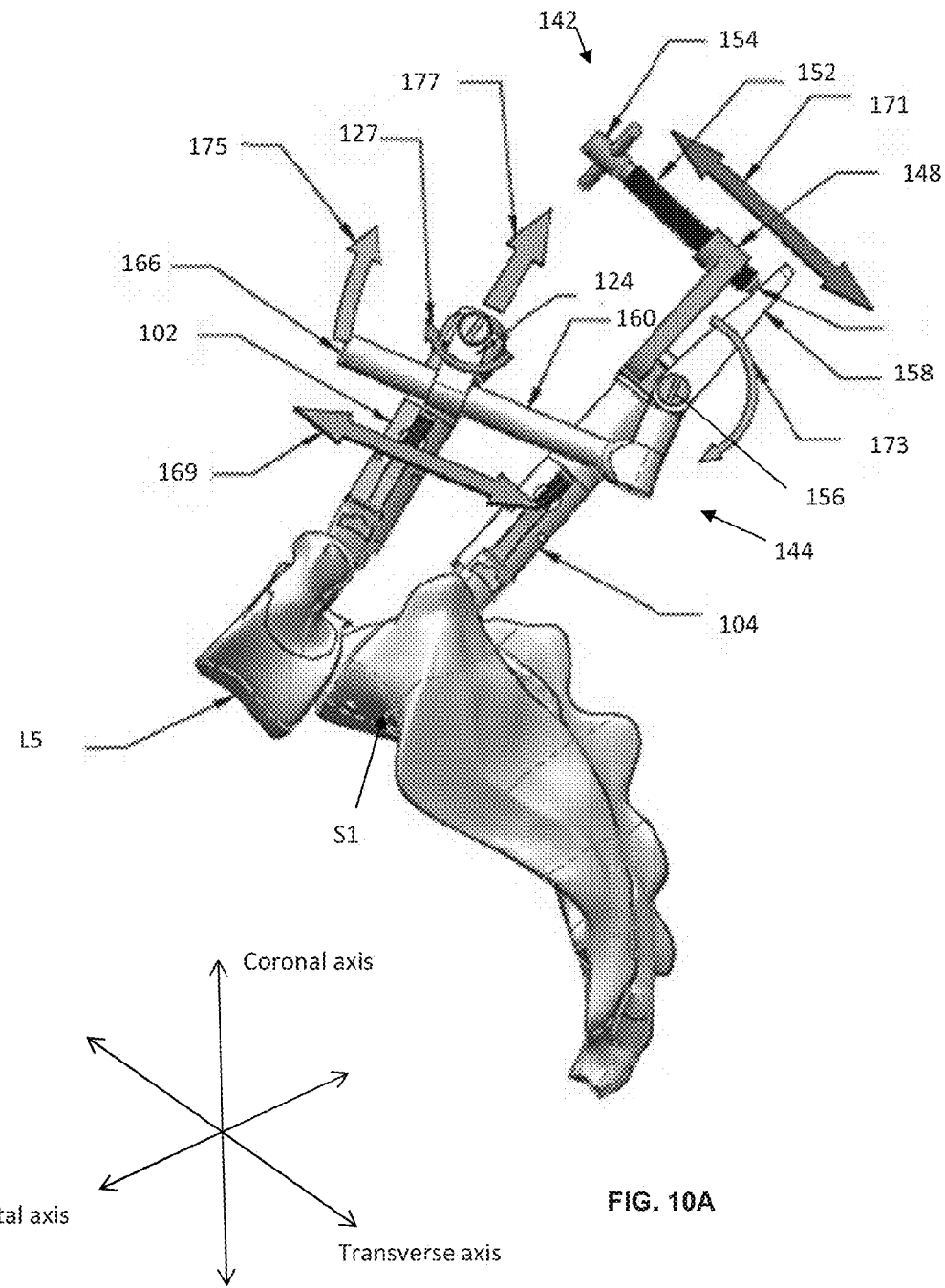
FIG. 10A is a side view of the right side of the system prior to positioning a L5 vertebra of the spine relative to a S1 level of the sacrum according to the principles of the present disclosure.

Referring now to FIG. 9, the two tower assemblies 102 and 104 of the right side of the system 100 are shown. Various features of the tower assemblies 102 and 104 provide multiple degrees of freedom that allow for rotational and translational movement in multiple planes. For example, the transfer ring 122 may allow for a rotation 123 of the second end 166 of the transfer member 144 in a first plane substantially parallel to the coronal plane. The transfer link 124 and post 126 may allow for a rotation 127 of the second end 166 of the transfer member 144 in a second plane substantially parallel to the sagittal plane. The bore 130 may allow for a rotation 125 of the second end 166 of the transfer member 144 in a third plane substantially parallel to the transverse plane. At the opposite end of the transfer member 144, the rotatable coupling at the first end 164 allows for a rotation 163 of the first end 164 in the plane substantially parallel to the coronal plane. The thru-bore 162 and second post 156 allow for a rotation 167 of the first end 164 in the plane substantially parallel to the sagittal plane. Sliding engagement between the transfer member 144 and the bore 130 allows for a translational movement 169 of the lumbar tower assembly 102 relative to the sacral tower assembly 104 in a plane substantially parallel to the sagittal plane, as shown in FIG. 10A. The lumbar tower assembly 102 may also be positioned anteriorly-posteriorly as the second end 166 of the transfer member transfers force applied by the load applicator 142.

Figure 10B:
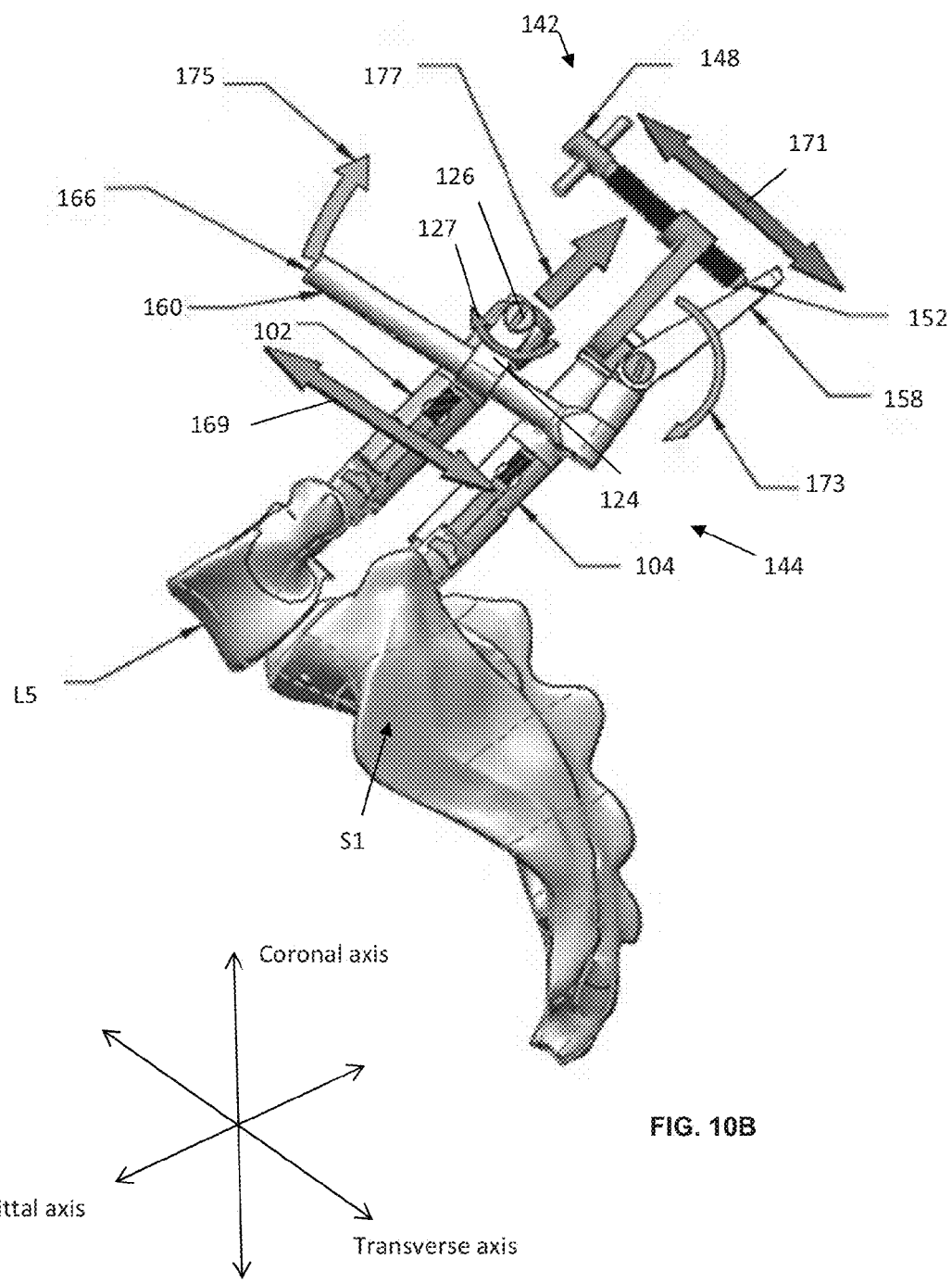
FIG. 10B is a side view of the right side of the system after positioning the L5 vertebra of the spine relative to the S1 level of the sacrum according to the principles of the present disclosure.

In FIGS. 10A and 10B, the system 100 may be used to correct spondylolisthesis at the L5-S1 level of the spine. For example, in FIG. 10A, the L5 vertebra has slipped forward or anteriorly from the S1 level of the sacrum. The slippage may occur due to degeneration of disc material between the L5 and S1 levels. The slippage may occur from a fracture of degeneration of the vertebral body and/or from fracturing of the L5 vertebra. In some cases, bone growth may occur on an upper surface of the S1 level due to rubbing from the L5 vertebra. The system 100 may be used to reposition the L5 vertebra into proper alignment with the S1 level and hold the L5 and S1 levels in place while permanent fixation is added in the form of fixation rods and set screws.

Continuing with FIG. 10A, the surgeon may rotate the load applicator 142 to apply a force on the receiving portion 158 of the transfer member 144. The load applicator 142 may advance 171 towards the receiving portion 158 in a plane substantially parallel to the sagittal plane as shown in FIG. 10A. As the load applicator 142 advances, the transfer member 144 rotates 173 about the post 156 also substantially in the plane parallel to the sagittal plane. Because the L5 vertebra may not be aligned with the S1 level of the sacrum in the sagittal plane, the linking portion 160 may also rotate 127 relative to the receiving portion 158 via the first end 164 as described above. As the force increases, the second end 166 of the linking portion 160 rotates proximally 175, thus pulling 177 the first tower assembly posteriorly 102 in line with the second tower assembly 104. The second end 166 slidably engages with the transfer link 124 to permit free translational movement 169 of the L5 vertebra in the sagittal plane. The transfer link 124 also rotates freely to accommodate the movement of the L5 vertebra.

Referring now to FIG. 10B, the load applicator 142 continues to advance 171 and apply force 173 to pull the L5 level into proper alignment with the S1 level. As the L5 level is positioned posteriorly, the sliding engagement 169 of the linking portion 160 with the transfer link 124 and rotatable connection 127 at the transfer link 124 and post 126 allow the L5 vertebra to follow a path of least resistance. Once the vertebra L5 is properly aligned with the S1 level of the sacrum, the rods 30 may be inserted into the receiving portions 20 of the screws 10 and 12 as shown in FIG. 1. Each tower assembly 102 and 104 may also be cannulated to permit insertion of setscrews within the receiving portions 20 of the screw 10 and 12 to permanently secure the L5-S1 level. Additionally, a spacer or other interbody device may be secured between the L5 vertebra and S1 level of the sacrum. Bone material may be inserted with the spacer or interbody device to promote bone fusion and bone growth to permanently fuse the L5-S1 level.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A system for reducing deformities in the spine, comprising:
    a first tower assembly including a first mount and a second tower assembly including a second mount, wherein the first mount is operably coupled to the proximal end of the first tower assembly, and the second mount is operably coupled to the proximal end of the second tower assembly;
    a load reduction arm including a central shaft, and the load reduction arm operably coupled to the first mount and translatable with the second mount to transmit a leverage and cause relative movement of the first tower assembly from the second tower assembly from an unreduced state into a reduced state,
    wherein the second mount includes a reduction drive shaft that is operably coupled with a drive shaft bore mounted on the proximal end of the second mount, wherein the reduction drive shaft includes a substantially threaded portion along the exterior of the reduction drive shaft to operably couple with a threaded portion along the interior of the drive shaft bore,
    wherein the first end of the load reduction arm is rotatably coupled to the distal end of the first mount, and the central shaft of the load reduction arm is operably coupled to the reduction drive shaft, such that distal movement of the reduction drive shaft causes the first end of the load reduction arm to move upwards and the first mount to move along its vertical axis into the reduced state,
    wherein the first mount includes a load transfer ring on the proximal end of the first mount to secure the first mount to the first tower assembly, and the second mount includes a load transfer ring for securing the second mount on the proximal end of the second tower assembly,
    wherein the distal end of the reduction drive shaft operably engages a distraction slide lock on the distal end of the second mount, the first end of the distraction slide lock is rotatably coupled with the distal end of the second mount, whereby the second end of the distraction slide lock is rotated by the advancement of the reduction drive shaft,
    wherein the distraction slide lock includes a distraction trigger operably coupled on the second end of the distraction slide lock, wherein the distraction trigger includes a locking feature as to lock the distraction slide lock with the central shaft of the load reduction arm.

2. The system of claim 1, wherein the distraction trigger is operably coupled with a locking tube displaced within a lock bore that traverses the bottom portion of the distraction slide lock;
    the locking tube includes a central lumen traversing the length of the locking tube, a recess opening traversing the surface and communicating with the central lumen, and the load reduction arm is coaxially displaced within the locking tube and translatable therein; and
    the locking feature operably engages the recess opening and traverses the thickness of the locking tube as to mate with the load reduction arm and lock the first tower assembly and the second tower assembly into a locked state.

3. The system of claim 2, wherein the load reduction arm includes a ratcheted portion along the central shaft to the second end of the load reduction arm, wherein the ratcheted portion mates with the locking feature to prevent longitudinal movement of the load reduction arm through the locking tube in the locked state.

4. The system of claim 3, wherein the load reduction arm includes a length L1 that is determined by the length between vertebrae to be distracted.

5. The system of claim 4, wherein the proximal end of the first mount and the second mount includes a trigger operably coupled with the load transfer ring as to lock the proximal end of the first tower assembly with the first mount and lock the proximal end of the second tower assembly with the second mount.

6. The system of claim 5, wherein the first tower assembly is operably coupled with a first screw and the second tower assembly is operably coupled with a second screw.

7. A method of displacing vertebrae, comprising:
locking a first screw within a first tower assembly and a second screw in a second tower assembly, wherein the first screw is associated with a first vertebrae and the second screw is associated with a second vertebrae, and the first and second vertebrae are separated by a height H and a length L;
attaching a first mount to the first tower assembly and a second mount to the second tower assembly, wherein a load reduction arm operably couples the first mount and the second mount in an unreduced state, and the second mount includes a reduction drive shaft operably coupled with the load reduction arm;
reducing the height H of the first vertebrae relative to the second vertebrae by longitudinally moving the reduction drive shaft to leverage the load reduction arm and displace the first mount along its vertical axis,
decreasing the length L between the first vertebrae and the second vertebrae by reducing the distance between the first mount and the second mount by placing a distractor between the first mount and second mount and applying a distraction load to cause the locking tube to move until a stopping feature on the locking tube abuts the second end of the distraction slide lock; and
locking the load reduction arm into a locked state on the second mount, wherein the load reduction arm is locked into place by a locking tube and a distraction slide lock operably coupled with the distal end of the second mount,
wherein a distraction trigger is operably coupled with the distraction slide lock and the locking tube, and the distraction trigger engages a ratcheted portion on the load reduction arm.

* * * * *